United States Patent [19]

Kohl, Jr.

[11] 3,960,800
[45] June 1, 1976

[54] ACETOXYSILOXANE ADHESION PROMOTER AND PRIMER COMPOSITION

[75] Inventor: Charles F. Kohl, Jr., Midland, Mich.

[73] Assignee: Dow Corning Corporation, Midland, Mich.

[22] Filed: Dec. 16, 1974

[21] Appl. No.: 533,102

[52] U.S. Cl................. 260/32.8 SB; 106/287 SB; 260/33.6 SB; 260/33.8 SB; 260/46.5 G; 260/46.5 UA
[51] Int. Cl.²............................................ C08K 5/07
[58] Field of Search............... 260/448.2 Q, 46.5 G, 260/46.5 UA, 33.6 SB, 33.8 SB, 32.8 SB; 106/287 SB

[56] References Cited
UNITED STATES PATENTS

| | | | |
|---|---|---|---|
| 3,061,575 | 10/1962 | Russell | 260/46.5 G |
| 3,240,731 | 3/1966 | Nitzsche et al. | 260/46.5 G |
| 3,719,635 | 3/1973 | Clark et al. | 260/46.5 G |
| 3,873,334 | 3/1975 | Lee | 260/46.5 G |

*Primary Examiner*—Melvyn I. Marquis
*Attorney, Agent, or Firm*—Roger H. Borrousch

[57] ABSTRACT

Reaction products, containing at least one vinyl group, which are obtained by mixing under anhydrous conditions

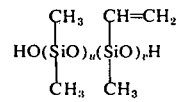

where $u$ is 0 to 15, $v$ is 0 to 7 and $u + v$ is 1 to 15 and

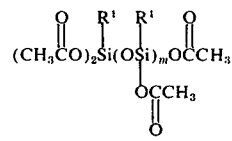

where $m$ is 0 to 5, and $R^1$ is methyl, ethyl, or vinyl are adhesion promoters which are useful in primer compositions. The primer compositions are organic solvent solutions with 50 to 99.9 weight percent organic solvent, with the balance being made up of 5 to 100 weight percent of the adhesion promoter, 0 to 50 weight percent of an alkylsilicate and 0 to 50 weight percent of an organotitanate. An example of a primer composition would be a solution of 90.0 weight percent inhibited 1,1,1-trichloroethane with 10.0 weight percent of equal weight amounts of an adhesion promoter where $u$ has an average value of 2, $v$ has an average value 1, and $m$ has an average value of about 0.7, ethylpoly-silicate and bis(acetylacetonyl)diisopropyltitanate. The primer compositions are useful in adhering room temperature vulcanizable silicone elastomers to substrates such as aluminum.

12 Claims, No Drawings

ACETOXYSILOXANE ADHESION PROMOTER AND PRIMER COMPOSITION

BACKGROUND OF THE INVENTION

1. Field of the Invention

This invention relates to an adhesion promoter and primer compositions prepared therefrom.

2. Description of Prior Art

Adhering silicone elastomers to various substrates is a continuing problem. There is an ever present need for better adhesion. With the changing substrates and silicone elastomers, the search for new methods of adhering the silicone rubber to substrates and for new materials to provide adhesion continues. One particular area wherein adhesion is required, is the application where a room temperature vulcanizable silicone elastomer is to be adhered to substrates, such as metals. Many of the prior art methods of adhering silicone rubber to substrates either are not suitable for today's materials, provide an insufficient bond strength or are too expensive because of the complex method or materials.

Keil in U.S. Pat. No. 2,751,314 teaches that silicone rubber can be adhered to the surface of a solid by depositing a continuous coating having 50 to 100 percent by weight of an organotitanate and 0 to 50 weight percent alkylpolysilicate, depositing over this coating another coating having 1 to 10 percent by weight alkylpolysilicate and 90 to 99.9 percent by weight of a toluene soluble organopolysiloxane, thereafter applying a silicone rubber such as a room temperature vulcanizable silicone rubber. While this method described by Keil does bond silicone rubber to a substrate, it requires two coatings to provide an adequate bond and it also shows that a silicone rubber layer containing alkylpolysilicate must be deposited over the titanate primer layer to achieve adequate bonding.

Harper in U.S. Pat. No. 2,979,420 teaches that a room temperature vulcanizing silicone rubber can be bonded to a surface by applying certain monoorganotriacyloxysilanes to the surface as a primer. Although this method is simple, the bonding achieved is insufficient in strength for many applications.

Chadha in U.S. Pat. No. 3,498,824 teaches that an alkoxyacyloxysilane can be used as a primer to adhere room temperature vulcanizing silicone rubber to metal substrates. Although the bond strength is improved with this primer compared to no primer, the bond strength is insufficient under many circumstances.

Young in U.S. Pat. No. 3,671,483 teaches that certain compositions are useful as primers for adhering silicone rubber to epoxy resin and polyurethane substrates. The compositions described contain alkylsilicates, organotitanates, solvent and a compound of the formula $CF_3CH_2CH_2(CH_3)_2SiOSiX_3$ where X is

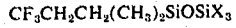
—$CH_2CH_2Si(OOCCH_3)_3$ or a hydrogen atom and at least one X is

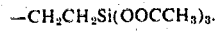
—$CH_2CH_2Si(OOCCH_3)_3$.

These primers provide useful adhesion, but have insufficient bond strength and those which contain silicon bonded hydrogen atoms form gas on storage.

Matherly in U.S. Pat. No. 3,714,109 teaches a mixture of an organic solvent, bis(acetylacetonyl)-diisopropyltitanate, an alkylpolysilicate and a mixture containing an organosiloxane having dimethylsiloxane units and methylhydrogensiloxane units and trimethylsiloxane units or dimethylhydrogensiloxane units and a modified organosiloxane having in addition to the above siloxane units,

$(CH_3COO)_3SiCH_2CH_2(CH_3)SiO$ units and

$(CH_3COO)_3SiCH_2(CH_3)_2SiO_{0.5}$ units. These primer compositions are suitable for adhering silicone rubber to substrates in certain applications but have insufficient bond strength for many applications and additionally have a potential to form hydrogen gas because of the presence of silicone-bonded hydrogen atoms.

Lee and Schulz in U.S. application Ser. No. 406,065 filed Oct. 12, 1973, now U.S. Pat. No. 3,914,199, and assigned to the assignee of this application, teach an organic solvent solution of an adhesion promoter prepared by mixing an organosiloxane having the formula

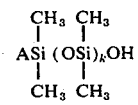

where A is vinyl or methyl and $k$ is 0 to 20 and an acetoxysilicon compound, and optionally, an alkyl polysilicate and an organotitanate. While these compositions provide excellent adhesion between silicone elastomers and various substrates, the organosiloxane is expensive to prepare.

Bruner in U.S. Pat. No. 3,035,016 teaches a compound of the formula

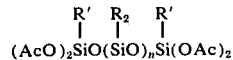
$(AcO)_2SiO(SiO)_nSi(OAc)_2$ where R and R' are monovalent hydrocarbon radicals, halogenated monovalent hydrocarbon radicals or cyanoalkyl radicals, Ac is a saturated aliphatic monoacyl radical of a carboxylic acid and $n$ is an integer of at least 5, but does not teach an adhesion promoter or a primer composition.

SUMMARY OF THE INVENTION

An object of this invention is to provide a composition suitable for providing strong adhesive bonds between room temperature vulcanizable silicone elastomers and substrates.

This invention relates to an adhesion promoter prepared by mixing hydroxy-endblocked polydiorganosiloxanes and an acetoxysilicon compound and to compositions consisting essentially of an adhesion promoter, an alkylsilicate and an organotitanate in an organic solvent solution. These compositions are useful as primers when applied to substrates such as metals, and thereafter during curing silicone elastomers on this primed surface. Silicone elastomers cured by the reaction of alkenylsiloxane, silicon-bonded hydrogen atoms and a platinum catalyst adhere particularly well whereas other primers do not provide as good adhesion for this type of silicone elastomer.

DESCRIPTION OF THE INVENTION

This invention relates to a composition under anhydrous conditions consisting essentially of an organic solvent solution of (a) a reaction product obtained by mixing under essentially anhydrous conditions (1) an organosiloxane of the formula

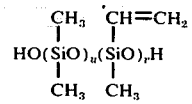

in which $u$ has an average value of from 0 to 15, $v$ has an average value of from 0 to 7, and the total of $u + v$ has an average value of from 1 to 15 inclusive where the organosiloxane species having values of $u + v$ above 15, if present, are in no more than minor amounts and (2) an acetoxysilicon compound of the formula

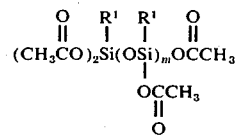

where $R^1$ is methyl, ethyl or vinyl and $m$ has an average value of from 0 to 5 inclusive, (1) and (2) being mixed in proportions to provide a ratio of acetoxy in (2) to hydroxyl in (1) of from 3/1 to 10/1, said reaction product containing at least one silicon-bonded vinyl radical (b) an alkyl silicate selected from the group consisting of ethylorthosilicate, propylorthosilicate, ethylpoly-silicate and propylpolysilicate, and (c) an organotitanate of the formula

Ti(OR²)₄ wherein each $R_2$ is a monovalent radical selected from the group consisting of alkyl radicals having from 1 to 5 carbon atoms and acetylacetonyl, (a) provides 5 to 100 weight percent, (b) provides 0 to 50 weight percent and (c) provides 0 to 50 weight percent where (a), (b), and (c) equals 100 weight percent, said organic solvent solution being from 50 to 99.9 weight percent of an organic solvent selected from the group consisting of ketones, halogenated hydrocarbons and hydrocarbons all having boiling points no greater than 150°C.

The compositions are prepared and stored under essentially anhydrous conditions, because the acetoxy functionality on the silicon compounds is reactive with moisture.

The reaction product (a) is prepared by mixing an organosiloxane and an acetoxysilicon compound under anhydrous conditions, either one or both of which has a silicon-bonded vinyl radical. The organosiloxane (1) has a formula

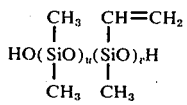

where $u$ has an average value of from 0 to 15 and $v$ has an average value of from 0 to 7. It is to be understood that the values of $u$ and $v$ are average values but that most of the individual organosiloxane molecules that are present in (1) do not contain more than about 15 siloxane units. The preferred organosiloxane has a value for $v$ greater than zero and the total of $u + v$ is less than 8. A number of methods are known in the art for the preparation of the organosiloxanes of (1).

One method is taught by Leitheiser in U.S. Pat. No. 3,122,579 wherein a diorganosilanediol is reacted with diorganosilanes containing hydroylzable groups to produce mixed trisiloxanes. These trisiloxanes can be reacted with water to produce mixed trisiloxane diols of the formula (1). where $u + v = 3$. Condensation of some of the silanols will provide organosiloxanes where the average value of $u + v$ is greater than three.

Another method is described by Brown and Hyde in U.S. Pat. No. 3,162,662 wherein an organochlorosilane can be reacted with a hexaorganocyclotrisiloxane in the presence of acetonitrile and N,N-dimethylacetamide. For this invention, the organochlorosilane would be a dichlorosilane. This method provides a chlorine-endblocked diorganopolysiloxane which can then be hydrolyzed under mild hydrolysis conditions to the corresponding hydroxylendblocked diorganopolysiloxane. Another method well known in the art is mild hydrolysis of diorganodichlorosilanes, diacetoxydiorganosilanes or diorganodialkoxysilanes or mixtures of said silanes to prepare the organosiloxane (1). By mild hydrolysis conditions, it is to be understood that condensation of the newly formed silanols is controlled, where this can readily be accomplished, by use of buffered solutions to keep the pH about 7.

The acetoxysilicon compounds (2) have a formula

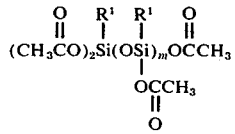

where $R^1$ is methyl, ethyl or vinyl and $m$ is 0 to 5. Specific examples of the acetoxysilicon compound (2) include methyltriacetoxysilane, vinyltriacetoxysilane, ethyltriacetoxysilane, and their mixtures and partial hydrolyzates thereof to provide the values of $m$ from above 0 to 5. These partial hydrolyzates of the silanes such as methyltriacetoxysilane can be readily obtained by slowly adding the necessary amount of water to the methyltriacetoxysilane to obtain the desired average value of $m$. Theoretically it requires one half mole of water per mole of acetoxy to hydrolyze and condense.

The organosiloxane (1) and the acetoxysilicon compound can be mixed in proportions to provide a ratio of acetoxy in (2) to hydroxyl in (1) of from 3/1 to 10/1, preferably from 3/1 to 7/1. As long as (1) and (2) are mixed under essentially anhydrous conditions and either one or both ingredients contain a silicon-bonded vinyl radical, the product obtained is useful as an adhesion promoter, particularly in the primer compositions. Better results are obtained if (1) is added to (2) although the reverse addition also gives an adhesion promoter. This reaction product can be prepared and used in making the primer compositions (prereacted method) or the organosiloxane (1) and the acetoxysilicone compound (2) can be added separately in making the primer composition (in situ method).

The alkylsilicates of (b) are known in the art and include ethylorthosilicate, propylorthosilicate, ethylpolysilicate and propylpolysilicate. These materials can be purchased commercially. The preferred alkylsilicate is ethylpolysilicate.

The organotitanates of (c) have a formula

$$Ti(OR^2)_4$$

where each $R^2$ is an alkyl radical of 1 to 5 carbon atoms such as methyl, ethyl, propyl, isopropyl, butyl, and amyl or acetylacetonyl. Specific examples include, tetrabutyltitanate, tetraisopropyltitanate, bis(acetylacetonyl)diisopropyltitanate, bis(acetylacetonyl)-diethyltitanate, bis(acetylacetonyl)dimethyltitanate and tetramethyltitanate. The preferred organotitanate (c) is bis(acetlacetonyl)diisopropyltitanate.

The organic solvents are those which have boiling points no greater than 150°C. and include ketones such as acetone, methylethylketone, methylisobutylketone, methylpropylketone, diethylketone, methyl-n-butylketone, ethylpropylketone, dipropylketone and butylethylketone; hydrocarbons such as hexane, pentane, heptane, octane, light naphthas and benzene and halogenated hydrocarbons, such as 1,1,1-trichloroethane, carbon tetrachloride, trichloroethylene, perchloroethylene, monochlorobenzene and trichlorotrifluoroethane.

The primer compositions can contain, in addition to (a), (b) and (c), other additives such as dyes to aid in the application of the primer composition and soluble platinum compounds to assist the curing reaction of the room temperature curing silicone elastomer that is subsequently applied to the primed substrate.

The soluble platinum compound is any of the platinum compositions that catalyze the addition of Si—H to carbon-carbon unsaturation sites, such as vinyl, and are soluble in the primer composition. An example is a solution of chloroplatinic acid in organopolysiloxane, as taught in U.S. Pat. No. 3,419,593.

There should be at least 1.0 part by weight platinum per million parts by weight of the primer composition. However, since impurities in the system may easily poison this small quantity of catalyst, it is preferred to employ from 10 to 200 parts by weight of platinum per million parts by weight primer composition. A greater amount of the platinum is not detrimental but does affect the cost and economic considerations thus suggesting the amounts mentioned.

The primer compositions are prepared by mixing the ingredients under essentially anhydrous conditions and the compositions are stored under anhydrous conditions until used. The order of mixing these ingredients is not narrowly critical, except that the best results are obtained when the organotitanate is added last. Preferably, the adhesion promoter is added to the organic solvent, followed by the platinum compound, the dye, the alkylsilicate, and the organotitanate if any. In those compositions wherein the reaction product is not used and the organosiloxane (1) and acetoxysilicon compound (2) are added separately, the order of addition of (1) and (2) is not critical.

The primer compositions can be prepared with 50 to 99.9 weight percent organic solvent. The best results are obtained with the more dilute solutions such as from 70 to 99 weight percent organic solvent. The remainder of the primer composition, 0.1 to 50 weight percent, is adhesion promoter (a) or a combination of (1) and (2) and, if present said soluble platinum compound, dye, alkylsilicate (b) and organotitanate (c), where these ingredients make up 100 weight percent of the remainder.

Primer compositions can be prepared where the ingredients other than organic solvent are 5 to 100 weight percent adhesion promoter (a) or a combination of (1) and (2) when added separately, from 0 to 50 weight percent alkylsilicate (b) and from 0 to 50 weight percent organotitanate (c). Preferably (a) is present in at least 25 weight percent, (b) is present in at least 25 weight percent and (c) is present in at least 25 weight percent.

The primer compositions are applied to the substrate surfaces to which the curable silicone elastomer is to be applied, in extremely thin layers. The primer composition can be applied by wiping, brushing, spraying and the like. The best results are obtained when as much of the primer composition is wiped off, after being applied, as possible. After the substrate has been primed, the solvent evaporates before the silicone elastomer is placed over the primed suface. The silicone elastomer can then be either cured at room temperature or heat vulcanized. The resulting cured silicone rubber is securely bonded to the substrate. This primer composition is particularly suited for metal substrates, such as aluminum, stainless steel, titanium and the like. The silicone elastomers can be either pourable compositions or flowable compositions which can be extruded from a tube or stiff compositions which are prepared from gum bases.

The primer compositions of this invention are particularly useful for silicone elastomers which cure by the addition reaction of silicon-bonded alkenyl radicals with silicon-bonded hydrogen atoms in the presence of a platinum catalyst. These silicone elastomers are known to the art and are available commercially in many forms.

The following examples are presented for illustrative purposes only and should not be construed as limiting the present invention which is properly delineated in the claims.

EXAMPLE 1

A hydroxyl-endblocked polydiorganosiloxane, 2004 grams containing an average of two dimethylsiloxy units and an average of one methylvinylsiloxy unit, 11 percent by weight silicon-bonded hydroxyl radicals and 10 percent by weight silicon-bonded vinyl radicals was slowly mixed uder anhydrous conditions with a mixture of methyltriacetoxysilane and ethyltriacetoxysilane, 2,724 grams (12.90 moles). This reactant ratio provided a OAc/OH ratio of 3.0. The mixing process took two hours and the exothermic reaction caused a temperature rise to about 70° from 21°C. The resulting mixture was devolatilized at a temperature of 91°C. and a pressure of 15 mm. of mercury to remove the by-product acetic acid. The residue was stored in a sealed container.

EXAMPLE 2

A hydroxyl-endblocked polymethylvinylsiloxane, containing an average of seven methylvinylsiloxy units 10.9 grams, was added slowly to a mixture of methyltriacetoxysilane and ethyltriacetoxysilane, 10.0 grams. The resulting adhesion promoter with its b-produced acetic acid was stored in a closed container.

EXAMPLE 3

In a three liter flask, 1838 grams of methyltriacetoxysilane was heated to about 40°C. This silane was stirred rapidly while 62.4 ml of water was slowly added from an additional funnel. After the first few milliliters, the temperature was reduced with an ice bath. The total addition time was about one hour. Volatile materials were removed under reduced pressure. The resulting partial hydrolyzate had a formula

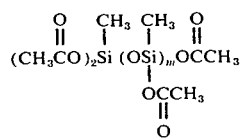

wherein $m$ had an average of about 0.7.

The next three examples illustrate the preparation of primer compositions using the in-situ method or the prereacted method.

EXAMPLE 4

A primer composition was prepared according to the in-situ method by adding to dry Chlorothene (Trademark of the Dow Chemical Company, Midland, Michigan for an inhibited 1,1,1-trichloroethane), 10 grams, the partial hydrolyzate of methyltriacetoxysilane of Example 3, 1.0 gram, the hydroxyl-endblocked polydiorganosiloxane of Example 1, 0.5 gram, ethylpolysilicate, 1.0 gram and bis-(acetyl-acetonyl)diisopropyltitanate, 1.0 gram. The product was stored in a sealed container to prevent premature reaction with moisture.

EXAMPLE 5

A primer composition was prepared by the prereacted method by adding to dry Chlorothene, 27 grams, the adhesion promoter of Example 2, 1 gram, ethylpolysilicate, 1 gram and bis(acetylacetonyl)diisopropyltitanate, 1 gram. The product was stored in a sealed container to prevent premature reaction with moisture.

EXAMPLE 6

A primer composition was prepared by adding to dry methylisobutyl ketone, 57 grams, the adhesion promoter of Example 1, 1.0 gram (except that a higher molecular weight version of the polydiorganosiloxane with a hydroxyl content of 3 percent by weight and enough of the acetoxy compound to give an acetoxy to hydroxy ratio of about 5.0 was used), ethylpolysilicate, 1.0 gram, bis(acetylacetoxyl)diisopropyltitanate, 1.0 gram, and a soluble platinum catalyst (as taught by U.S. Pat. No. 3,419,593) consisting of an organopolysiloxane solution of chloroplatinic acid, (0.65% by weight platinum), 0.3 grams, thereby providing 32 parts of Pt for every 1 million parts of primer composition by weight. The resulting primer composition was stable when stored under anhydrous conditions.

The next two examples illustrate the usefulness of the primer composition of this invention.

EXAMPLE 7

Primer compositions were prepared by the prereacted method (unless indicated) by mixing under essentially anhydrous conditions in Chlorothene (Trademark of the Dow Chemical Company, Midland, Michigan for an inhibited 1,1,1-trichloroethane), unless otherwise indicated, ethylpolysilicate, bis(acetylacetonyl)-diisopropyltitanate, and an adhesion promoter, prepared from the hydroxyl compound and the acetoxy compound indicated in Table I and described below. In the prereacted method of primer preparation the adhesion promoter was prepared according to the method of Example 1 or 2 and then added to the solvent followed by the addition of ethylpolysilicate and organotitanate (see Example 5). In the in-situ method the acetoxy compound and the hydroxyl compound were added to the solvent to prepare the adhesion promoter in-situ followed by the addition of ethylpolysilicate and organoitanate (see Example 4). The weight percentage of ingredients used and the resulting acetoxy/hydroxy ratio in the reactants are indicated in Table I. The primer compositions were wiped on aluminum test panels, then rubbed vigorously to remove any excess amounts, allowed to stand at least one hour before applying a silicone elastomer to make the adhesion test panels. The silicone elastomer was the same in each test and was basically a diorganopolysiloxane containing methyl and vinyl radicals, an organosilicon compound containing siliconbonded hydrogen atoms and a platinum catalyst. The test panels were prepared and tested in accordance with the procedure set forth in ASTM-Designation: C 273-61 (Reapproved 1970). The silicone elastomer was cured on the panel by heating for 1 hour at 150°C. or, as indicated in the footnotes, at room temperature for the specified length of time. The results for this lap shear adhesion test were reported in percent cohesive failure and in pounds per square inch, which was converted to kilograms per square centimeter for this application, and were the average of two or more tests unless otherwise indicated. The test results were as shown in Table I.

Table I

| Primer Composition (weight percent) | | Reactive Ingredients (weight percent) | | | Adhesion Promoter Ingredients | | | Lab Shear Test | |
| --- | --- | --- | --- | --- | --- | --- | --- | --- | --- |
| Chlorothene | Reactive Ingredients | Adhesion Promoter | Ethylpoly-silicate | Organo-Titanate | Hydroxy Compound | Acetoxy Compound | Acetoxy Hydroxy | Adhesive Strength kg/cm² | % Cohesive Failure |
| None | None | None | None | None | None | None | None | 0.63(1) | 0 |
| None | None | None | None | None | None | None | None | 0.39(1) (2) | 0 |
| 90.0 | 10.0 | 33.3 | 33.3 | 33.3 | A | III | 3.1 | 62.2 | 100 |

Table I-continued

| Primer Composition (weight percent) | | Reactive Ingredients (weight percent) | | | Adhesion Promoter Ingredients | | | Lab Shear Test | |
|---|---|---|---|---|---|---|---|---|---|
| Chlorothene | Reactive Ingredients | Adhesion Promoter | Ethylpoly-silicate | Organo-Titanate | Hydroxy Compound | Acetoxy Compound | Acetoxy Hydroxy | Adhesive Strength kg/cm² | % Cohesive Failure |
| 94.2 | 5.8 | 42.9 | 28.6 | 28.6 | A | III | 3.0 | 52.9 | 100 |
| 94.7 | 5.3 | 37.5 | 31.3 | 31.3 | A | III | 3.0 | 47.5 | 100 |
| 95.0 | 5.0 | 33.3 | 33.3 | 33.3 | A | III | 3.0 | 48.2 | 100 |
| 95.3 | 4.7 | 28.6 | 35.7 | 35.7 | A | III | 3.0 | 51.1 | 100 |
| 94.5(3) | 4.5 | 30.3(4) | 30.3 | 30.3 | A(5) | III | 5.0 | 51.5 | 100 |
| 94.2 | 5.8 | 42.9 | 28.6 | 28.6 | A | I | 3.0 | 44.6 | 100 |
| 94.7 | 5.3 | 37.5 | 31.3 | 31.3 | A | I | 3.0 | 49.6 | 100 |
| 95.0 | 5.0 | 33.3 | 33.3 | 33.3 | A | I | 3.0 | 47.2 | 100 |
| 95.3 | 4.7 | 28.6 | 35.7 | 35.7 | A | I | 3.0 | 48.7 | 100 |
| 74.1 | 25.9 | 42.9 | 28.6 | 28.6 | A | II | 3.1 | 61.5(6) | 100 |
| 74.1 | 25.9 | 42.9 | 28.6 | 28.6 | A | II | 3.1 | 51.7(6)(2) | 94 |
| 90.0 | 10.0 | 33.3 | 33.3 | 33.3 | B | II | — | 57.3 | 94 |
| 90.0 | 10.0 | 33.3 | 33.3 | 33.3 | B | II | — | 52.9(2) | 86 |
| 90.0 | 10.0 | 33.3 | 33.3 | 33.3 | B | III | — | 64.1 | 100 |
| 90.0 | 10.0 | 33.3 | 33.3 | 33.3 | B | III | — | 47.1(2) | 75 |
| 94.5(3) | 4.5 | 30.3(4) | 30.3 | 30.3 | B | III | 3.0 | 47.6 | 90 |
| 95.0 | 5.0 | 33.3 | 33.3 | 33.3 | C | I | 3.0 | —(8) | —(8) |
| 94.5(3) | 4.5 | 30.3(4) | 30.3 | 30.3 | C(7) | III | 3.0 | 38.0 | 20 |

(1) Only one panel tested.
(2) Cure was 7 days at rooom temperature.
(3) Solvent was methylisobutylketone.
(4) Reactive ingredients contains 9.1% by weight of a platinum catalyst solution containing a platinum concentration of 0.65% by weight platinum in the catalyst solution and yielding a concentration of 32 ppm by weight platinum in the composition.
(5) A higher molecular weight, lower hydroxyl content, organosiloxane was used.
(6) Primer prepared by the in-situ method.
(7) For comparative purposes only.
(8) Qualitative measurements indicated adhesion to be as good as that obtained when hydroxy compound A and acetoxy compound III was used to form the adhesion promoter.

Hydroxyl-endblocked organosiloxane (average composition)

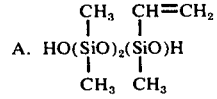

A. HO(SiO)₂(SiO)H with CH₃, CH=CH₂, CH₃, CH₃ substituents

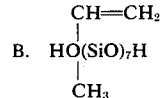

B. HO(SiO)₇H with CH=CH₂ and CH₃ substituents

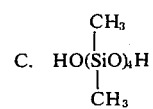

C. HO(SiO)₄H with CH₃ substituent

Acetoxysilicon compound

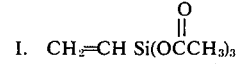

I. CH₂=CH Si(OCCH₃)₃ (with C=O)

III. CH₃Si(OCCH₃)₃ and CH₃CH₂SiOCCH₃)₃ mixture (with C=O groups)

EXAMPLE 8

Test panels were prepared and tested as described in Example 7, except the silicone elastomer contained 3,3,3-trifluoropropylmethylsiloxane units and methylvinylsiloxane units. This silicon elastomer was cured by the same mechanism as described in Example 7, namely, by using a silicon compound containing silicon-bonded hydrogen atoms and a platinum catalyst. The results were as shown in Table II. The materials used were the same for the primer composition as shown in Example 7.

Table II

| Primer Composition (weight percent) | | Reactive Ingredients (weight percent) | | | Adhesion Promoter Ingredients | | | Lab Shear Test | |
|---|---|---|---|---|---|---|---|---|---|
| Chlorothene | Reactive Ingredients | Adhesion Promoter | Ethylpoly-silicate | Organo-Titanate | Hydroxy Compound | Acetoxy Compound | Acetoxy Hydroxy | Adhesive Strength kg/cm² | % Cohesive Failure |
| None | None | None | None | None | None | None | None | 0.14 | 0 |
| None | None | None | None | None | None | None | None | 0.35(2) | 0 |
| None | None | None | None | None | None | None | None | 5.5 | 0 |
| 74.1 | 25.9 | 42.9 | 28.6 | 28.6 | A | II | 3.1 | 53.6 | 100(6) |
| 74.1 | 25.9 | 42.9 | 28.6 | 28.6 | A | II | 3.1 | 48.6(2) | 93(6) |
| 90.0 | 10.0 | 33.3 | 33.3 | 33.3 | A | III | 3.1 | 45.3 | 99 |
| 90.0 | 10.0 | 33.3 | 33.3 | 33.3 | B | II | — | 30.8 | 58 |
| 90.0 | 10.0 | 33.3 | 33.3 | 33.3 | B | II | — | 31.1(2) | 25 |
| 90.0 | 10.0 | 33.3 | 33.3 | 33.3 | B | III | — | 26.4 | 34 |
| 90.0 | 10.0 | 33.3 | 33.3 | 33.3 | B | III | — | 14.4(2) | 7 |

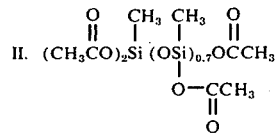

II. (CH₃CO)₂Si(OSi)₀.₇OCCH₃ with O—CCH₃ and O= substituents

That which is claimed is:
1. A composition consisting essentially of a reaction product obtained by mixing essentially anhydrous conditions 1. an organosiloxane of the formula $$HO(\underset{\underset{CH_3}{|}}{\overset{\overset{CH_3}{|}}{Si}}O)_u(\underset{\underset{CH_3}{|}}{\overset{\overset{CH=CH_2}{|}}{Si}}O)_vH$$

in which $u$ has an average value of from 0 to 15, $v$ has an average value of from 0 to 7 and the total of $u + v$ has an average of from 1 to 15 inclusive where the organosiloxane species having values of $u + v$ above 15, if present, are in no more than minor amounts and 2. an acetoxysilicon compound of the formula $$(CH_3C-O)_2Si(OSi)_mOCCH_3$$ (with $R^1$ groups and OCCH$_3$ as shown)

where $R^1$ is methyl, ethyl or vinyl and $m$ has an average value of from 0 to 5 inclusive, (1) and (2) being mixed in proportions to provide a ratio of acetoxy in (2) to hydroxyl in (1) of from 3/1 to 10/1, said reaction product containing at least one silicon-bonded vinyl radical.

2. The composition in accordance with claim 1 wherein the ratio of acetoxy in (2) to hydroxy in (1) is from 3/1 to 7/1.

3. The composition in accordance with claim 2 wherein $u$ is 2 and $v$ is 1.

4. The composition in accordance with claim 3 wherein $R^1$ is vinyl and $m$ is 0.

5. The composition in accordance with claim 3 wherein $R^1$ is methyl and $m$ has an average value of from 0.5 to 1.

6. The composition in accordance with claim 3 wherein the acetoxysilicon compound is a mixture of methyl-triacetoxysilane and ethyltriacetoxysilane.

7. The composition in accordance with claim 2 wherein $u$ is 0 and $v$ is 7.

8. The composition in accordance with claim 7 wherein $R^1$ is methyl and $m$ has an average value of from 0.5 to 1.0.

9. The composition in accordance with claim 7 wherein the acetoxy silicon compound is a mixture of methyl-triacetoxysilane and ethyltriacetoxysilane.

10. The composition in accordance with claim 2 where $u$ is 4 and $v$ is 0 and $R^1$ is vinyl and $m$ is 0.

11. A composition under anhydrous conditions consisting essentially of an organic solvent solution of
  a. the composition according to claim 1,
  b. an alkyl silicate selected from the group consisting of ethylorthosilicate, propylorthosilicate, ethylpolysilicate and propylpolysilicate, and
  c. an organotitanate of the formula $$Ti(OR^2)_4$$

wherein each $R^2$ is a monovalent radical selected from the group consisting of alkyl radicals having from 1 to 5 carbon atoms and acetylacetonyl
    a. provides 5 to 100 weight percent, (b) provides 0 to 50 weight percent, and (c) provides 0 to 50 weight percent where (a), (b, and (c), equal 100 weight percent, said organic solvent solution being from 50 to 99.9 weight percent of an organic solvent selected from the group consisting of ketones, halogenated hydrocarbons and hydrocarbons all having boiling points no greater than 150°C.

12. A composition under anhydrous conditions consisting essentially of an organic solvent solution prepared by mixing
  1. an organosiloxane of the formula $$HO(\underset{\underset{CH_3}{|}}{\overset{\overset{CH_3}{|}}{Si}}O)_u(\underset{\underset{CH_3}{|}}{\overset{\overset{CH=CH_2}{|}}{Si}}O)_vH$$

$u$ has an average value of from 0 to 15, $v$ has an average value of from 0 to 7 and the total of $u + v$ has an average value of from 1 to 15 inclusive where the organosiloxane species having values of $u + v$ above 15, if present, are in no more than minor amounts, 2. an acetoxysilicon compound of the formula $$(CH_3CO)_2Si(OSi)_mOCCH_3$$ (with $R^1$ groups and OCCH$_3$ as shown)

in which $m$ has an average value of from 0 to 5 inclusive and $R^1$ is methyl, ethyl, or vinyl, there being present at least one silicon-bonded vinyl radical in the combination of (1) and (2),
  b. an alkyl silicate selected from the group consisting of ethylorthosilicate, propylorthosilicate, ethylpolysilicate and propylpolysilicate, and
  c. an organotitanate of the formula $$Ti(OR^2)_4$$

wherein each $R^2$ is a monovalent radical selected from the group consisting of alkyl radicals having from 1 to 5 carbon atoms and acetylacetonyl, and
  (1) and (2) being present in amounts sufficient to provide a ratio of acetoxy in (2) to hydroxyl in (1) of from 3/1 to 10/1, a combination of (1) and (2) provides from 5 to 100 weight percent, (b) provides 0 to 50 weight percent, and (c) provides 0 to 50 weight percent where (1), (2), (b), and (c) equals 100 weight percent, said organic solvent solution being from 50 to 99.9 weight percent of an organic solvent selected from the group consisting of ketones, halogenated hydrocarbons and hydrocarbons all having boiling points no greater than 150°C.

* * * * *